United States Patent [19]

Takenouchi et al.

[11] Patent Number: 5,123,739
[45] Date of Patent: Jun. 23, 1992

[54] METHOD OF MONITORING CEMENT KILN AND THE APPARATUS THEREFOR

[75] Inventors: Takeyoshi Takenouchi, Oumiya; Masumi Nakagawa, Musashino, both of Japan

[73] Assignee: Mitsubishi Mining & Cement Company Ltd., Tokyo, Japan

[21] Appl. No.: 509,184

[22] Filed: Apr. 16, 1990

[30] Foreign Application Priority Data

Apr. 17, 1989 [JP] Japan .................................. 1-95412

[51] Int. Cl.$^5$ ............................................. G01J 3/42
[52] U.S. Cl. ........................................ 356/319; 356/45
[58] Field of Search .................. 356/319, 45; 432/106; 202/270, 100, 216

[56] References Cited

U.S. PATENT DOCUMENTS 2,166,824  7/1939  Runaldue ............................ 356/45
4,619,533 10/1986  Lucas et al. ........................ 356/45

OTHER PUBLICATIONS

Pyro Series Instructions (Chino) (no date).

*Primary Examiner*—F. L. Evans
*Assistant Examiner*—K. P. Hantis
*Attorney, Agent, or Firm*—Hoffman, Wasson & Gitler

[57] ABSTRACT

There is provided a method of monitoring a firing condition in a cement kiln, by measuring an intensity of spectrum of a radiation which radiation is emitted from a clinker being fired in a cement kiln, and processing the intensity of the spectrum to produce a parameter for monitoring the condition in the kiln, by correcting the intensity profile of the spectrum by interpolating a profile (range) which is deformed by the absorption with alkali atom(s) in an atmosphere of the kiln. Further, the absorption intensity of the spectrum at a sodium absorption wavelength and potassium absorption wavelength should be continuously measured and corrected by interpolating so as to produce a parameter for monitoring. An apparatus for monitoring a cement kiln, comprises an optical head collector equipped at a kiln hood of the kiln, to collect a radiation from a clinker being fired in the kiln, an optical fiber for transmitting the collected radiation, a spectrophotometer for analyzing the collected radiation, which is connected to said optical fiber, and, a processor for processing said intensity of the spectrum measured by said spectrophotometer, outputting the processed data, and controlling the operation of the spectrophotometer. Further, the apparatus has said optical collector and said optical fiber mounted respectively on each of a plurality of the cement kilns, and a transfer switch(s) for selecting an optical head and an optical fiber connecting the kiln to be monitored, and then, a plurality of the cement kilns can be monitored.

4 Claims, 6 Drawing Sheets

METHOD OF MONITORING CEMENT KILN AND THE APPARATUS THEREFOR

FIELD OF THE INVENTION

The present invention relates to a method of monitoring a cement kiln and the apparatus therefor. Particularly, it relates to the method of determining the information from the cement kiln, so as to monitor the sintering condition in the kiln, and the apparatus for picking or measuring.

DESCRIPTION OF THE PRIOR ART

The cement kiln has been controlled by monitoring a kiln torque, a temperature of the sintering zone, the concentrations of $NO_x$, and $O_2$ in the exit gas from the kiln. Various types of pyrometer to detect or determine the temperature at the firing zone in the kiln have been developed. Among them, most reliable one is two color pyrometer, but it does not consider the change of emissivity. Therefore, it does not establish the stability of the measurement. The composition of the raw materials for the kiln may be changed, and the firing condition may be changed by falling a coating attached on the refractory wall of the kiln, i.e. when the steady state may be broken or when the non-steady state may transfer into the steady state, or during the recovery time to the steady state, the dusty (powdery) component content in the clinker, or the powder is increased and will enter into the kiln atmosphere with air blow for combustion of fuel, which will produce the dusty atmosphere in the kiln. Therefore, the radiation from the kiln may be screened by such dusty atmosphere, and then, it will be impossible to measure or determine the temperature in the kiln or to monitor the firing condition in the kiln.

In the prior art, the measurement is corrected in view of the concentrations of $NO_x$ and $O_2$ in the kiln exit gas which have been separately measured. However, such correction can not cope with the rapid change of the firing condition in the kiln or the sintering quality of the clinker and then the measurement will be instable to monitor or control the firing condition in the kiln.

Therefore, it has been desired to find the method of monitoring or detecting the firing condition in the kiln with high accuracy, so as to operate the kiln with fine stability, even when the atmosphere in the kiln contains dusty powder of the clinker.

SUMMARY OF THE INVENTION

With the foregoing considerations in mind, the present invention contemplates the provision of the method of monitoring a cement kiln, for the purpose of controlling finely and correctly the firing operation and establishing stable operation, by measuring or determining the temperature with high accuracy, even when the atmosphere in the kiln contains dusty powder of the clinker.

It is an object of the present invention to provide an apparatus for monitoring the firing condition in the kiln, with fine accuracy, i.e. determining finely the temperature of the fired material in the kiln, or the alkali spectrum of the radiation in the kiln, so as to enable to control finely the operation of firing and manufacturing the cement.

It is another object of the present invention to provide a method of operating stably the cement kiln, by monitoring the firing condition in the kiln by measuring a line spectrum absorption intensity at sodium absorption wavelength, and potassium absorption wavelength (of sodium and potassium spectrum).

BRIEF DESCRIPTION OF THE DRAWINGS

FIGS. 7 A and B are schematic illustrations of system for monitoring a plurality of the cement kilns, by using optical fibers and connecting and switching transmitter, in accordance with the inventive monitoring apparatus.

DETAILED DESCRIPTION OF PREFERRED EMBODIMENTS

In accordance with the present invention, a cement kiln can be monitored so as to establish a stable firing condition, by measuring accurately and correctly the temperature in the kiln sintering zone (and the absorption intensity of alkali spectrum). First of all, an intensity of spectrum of a radiation which radiation is emitted from a clinker being fired in a cement kiln is measured, and the measured intensity of the spectrum absorption is processed so to be used as a parameter for monitoring the condition in the kiln, by correcting the intensity profile of the spectrum by interpolating a profile (range) which is deformed by the absorption with alkali atom(s) in an atmosphere of the kiln.

Further, the absorption intensities of the spectrum at a sodium absorption wavelength and potassium absorption wavelength should be continuously measured and corrected by interpolating so as to produce a parameter for monitoring.

An apparatus for monitoring a cement rotary kiln, comprises an optical head (sensor) equiped at a kiln hood of the kiln, to gather a radiation from a clinker being fired in the kiln; an optical fiber for transmitting the received radiation; a spectrophotometer for analysing the gathered radiation, which is connected to said optical fiber, and, a processor for processing said intensity of the spectrum measured by said spectrophotometer, outputting the processed data, and controlling the operation of the spectrophotometer.

Further, the apparatus can have a plurality of the optical heads and the optical fibers mounted respectively on each of a plurality of the cement kilns, and transfer switch(s) for selecting an optical head and an optical fiber connecting the kiln to be monitored, and then, a plurality of the cement kilns can be monitored. By switching the transfer switch intermittently, assembled plural kilns can be monitored by the inventive monitoring apparatus.

"Intensity of alkali spectrum" which should be measured or determined by the inventive monitoring method means "the difference between the actually measured spectrum intensity $I(\lambda i)$ of alklai (sodium or potassium) and the radiation intensity $I(\lambda b)$ at a sodium and potassium spectrum wavelength assuming that alkali does not exist. When the difference between $I(\lambda i)$ and $I(\lambda b)$ is negative, alkali spectrum is absorption spectrum. When the difference is positive, alkali spectrum is emission (luminescence) spectrum. In the other words, "intensity of alkali spectrum" means "spectrum intensity which is measured by analysing a radiation received in a spectrophotometer into spectrum of wavelength, measuring the intensity at the lines of sodium absorption and potassium absorption, and then measuring the values of the intensity of the line spectrum at the appropriate wavelength of the neighborhood to the said absorption lines and interpolating the intensity of the wavelength corresponding to each of the absorption wavelength lines by calculating from the values of the intensity of the neighborhood, and the difference between the actually measured intensity and the interpolated value being intensity of alkali spectrum".

In accordance with the present invention, a line spectrum absorption intensity is measured by a spectrophotometer, especially for sodium absorption line and potassium absorption line. Then, the values of the intensity at the sodium absorption line and potassium absorption lines can be used as the parameter for monitoring the firing condition in the kiln, or controlling the operation of the kiln.

In an ordinary cement kiln, there are sodium and potassium atoms vaporized between the firing zone and the kiln hood, which atoms emit the radiation, and then the line spectrum of the radiation is measured. The change of the intensity is used as a parameter for controlling the cement kiln.

When the kiln is operated in a steady state, the line spectrum of sodium and potassium will be absorption spectrum. When the operation of the kiln is instable or in a non-steady state, the absorption will be weaker or the emission spectrum is resulted. The correct theory of the above mentioned phenomenon is unclear, and generally speaking, most of alkali elements contained in the materials are vaporized between the inlet of the kiln and the firing zone, and the portions thereof can be present in a cooling zone of the kiln outlet and the high temperature portion of the clinker cooler. Air heated by heat exchange in the clinker cooler can be recovered as combustion air of the fuel in the cement kiln. Such recovered air contain the vaporized sodium and potassium vaporized at the high temperature portion of the clinker cooler.

Figure 6:
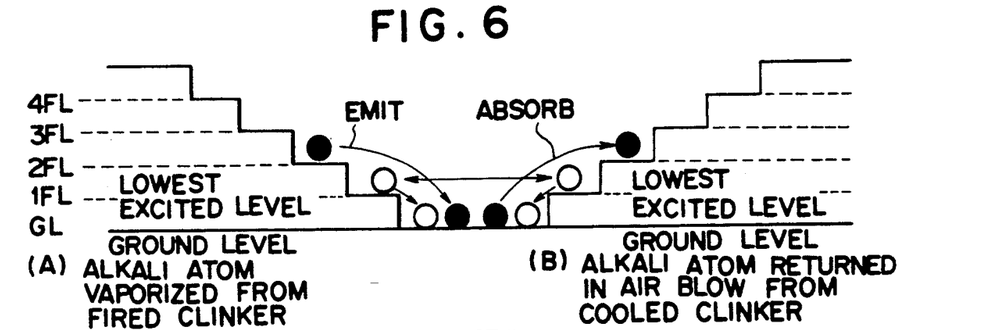
FIG. 6 illustrates schematically the energy level structure of alkali atom existing in the firing in the kiln, wherein electrons in the alkali atom are exited, radiation emitting and being absorbed.

FIG. 6 illustrates schematically the energy level structure of alkali atom existing in the firing zone in the kiln, wherein electrons in the alkali atom are exited, radiation emitting and being absorbed in order to explain the phenomenon of an exited state, emission and absorption of alkali atoms.

The structure of electron energy levels in alkali atom vaporized in the firing zone in the kiln is as shown in FIG. 6 (A), and the electrons in the vaporized alkali atoms are at the energy level higher than the ground state, e.g. not less than 1 FL level, and after light equivalent to the difference of energy level emits, the electrons return to the ground state.

The state of electron energy levels in the alkali atoms which are contained in the recovered air as secondary air by heat exchange at the clinker cooler is as shown in FIG. 6 (B), in which the atoms are mostly in the lower energy level, i.e. the ground state, or metastable state, and when they absorb the light (energy) emitting from the alkali atoms as shown in FIG. 6 (A), the electrons are excited to the higher level, e.g. higher than 1 FL.

It can be presumed that when the steady state is maintained, the measured alkali spectrum intensity will be absorption spectrum, and on the other hand, when the kiln is operated in non-steady state, the absorption spectrum intensity will be smaller because the light emitted by alkali atoms [refer to FIG. 6 (B)] will be weaken.

The alkali contents in the raw materials are continuously changed, and the alkali contents present in the firing zone are changed, and then, it was confirmed as mentioned in the below Examples that the change of those contents will not affect the absorption intensity, but will affect the width of the absorption spectrum (the width of the absorption peak).

Sodium atoms have absorption peak at 589.6 nanometer, and potassium atoms have two absorption peaks at 766.5 nanometer and 769.9 nanometer. Therefore, the line spectrum absorption intensity should be measured at such wavelength positions so as to monitor the firing condition in the kiln.

The present invention is deviced for monitoring the operation of the cement kiln, but it can be said to be found that the line spectrum absorption intensity of vaporized atoms (or molecules) can be utilized so as to monitor the other high temperature furnace such as a blast furnace.

Figure 7A:
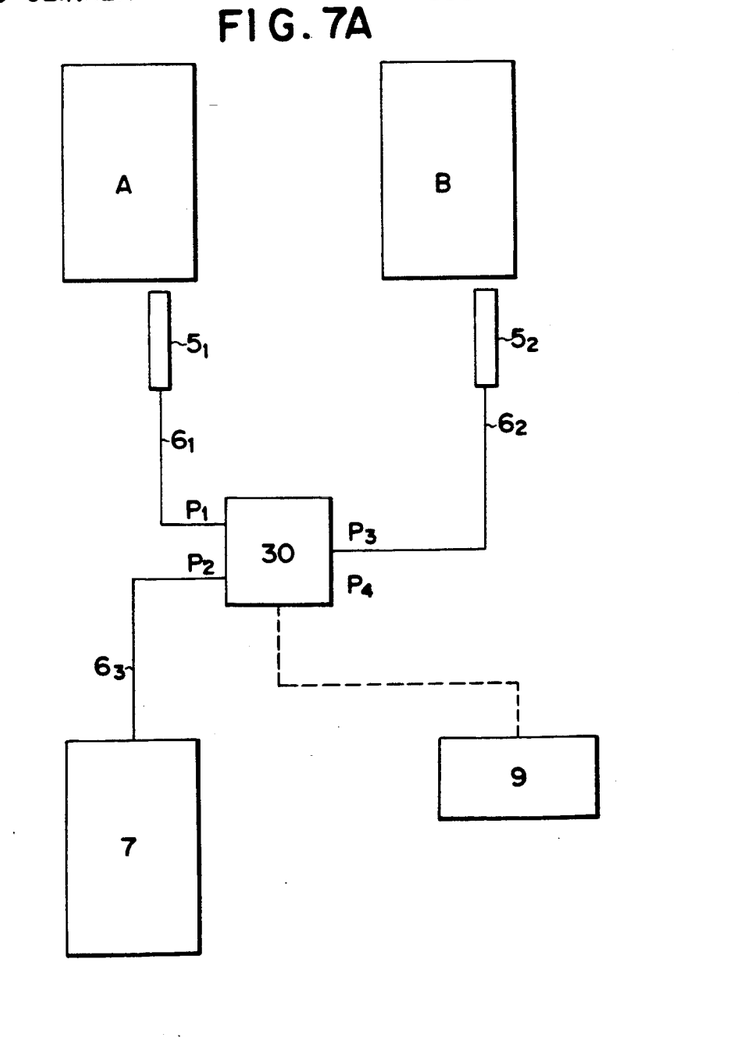
Figure 7B:
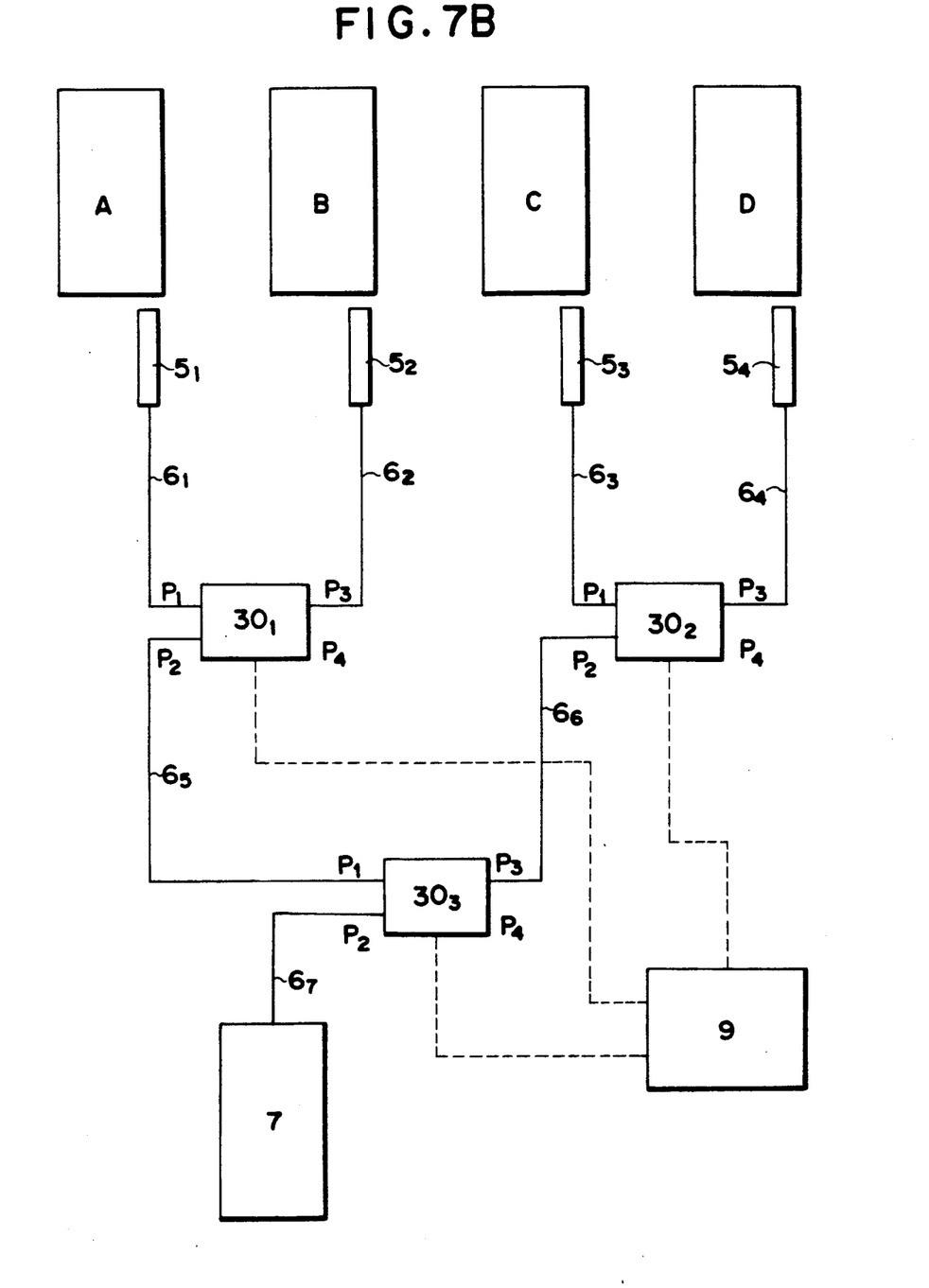

FIGS. 7 A and B are schematic illustrations of system for monitoring a plurality of the cement kilns such as A, B, C and D, by using optical fibers $P_1$ to $P_4$, and connecting and switching transmitters such as $30_1$ to $30_3$, in accordance with the inventive monitoring apparatus.

The switching transmitters can change over optical fibers $6_1$ to $6_4$ for monitoring the target kilns. Therefore, only one monitoring apparatus 7 can detect or monitor a plurality of the cement kilns. The radiations transmitted through a plurality of optical heads and fibers can be entered in order or intermittently into one monitoring apparatus 7 by switching the switching transmitters such as $30_1$ to $30_3$ in a predetermined and optional time of pattern, and is measured by the monitoring apparatus 7.

In this specification, the intensity of alkali absorption spectrum is directly indicated, but the temperature can be determined from the calculation of the relation of the intensity with the temperature, and then, it is possible to display the temperature in the kiln, which has been determined or measured in accordance with the invention. This is included in the scope of the present invention.

The present invention is further illustrated by the following example to show the typical structure of the inventive monitoring apparatus essentially for the cement kiln, but should not be interpreted for the limitation of the invention.

EXAMPLE 1

Figure 1:
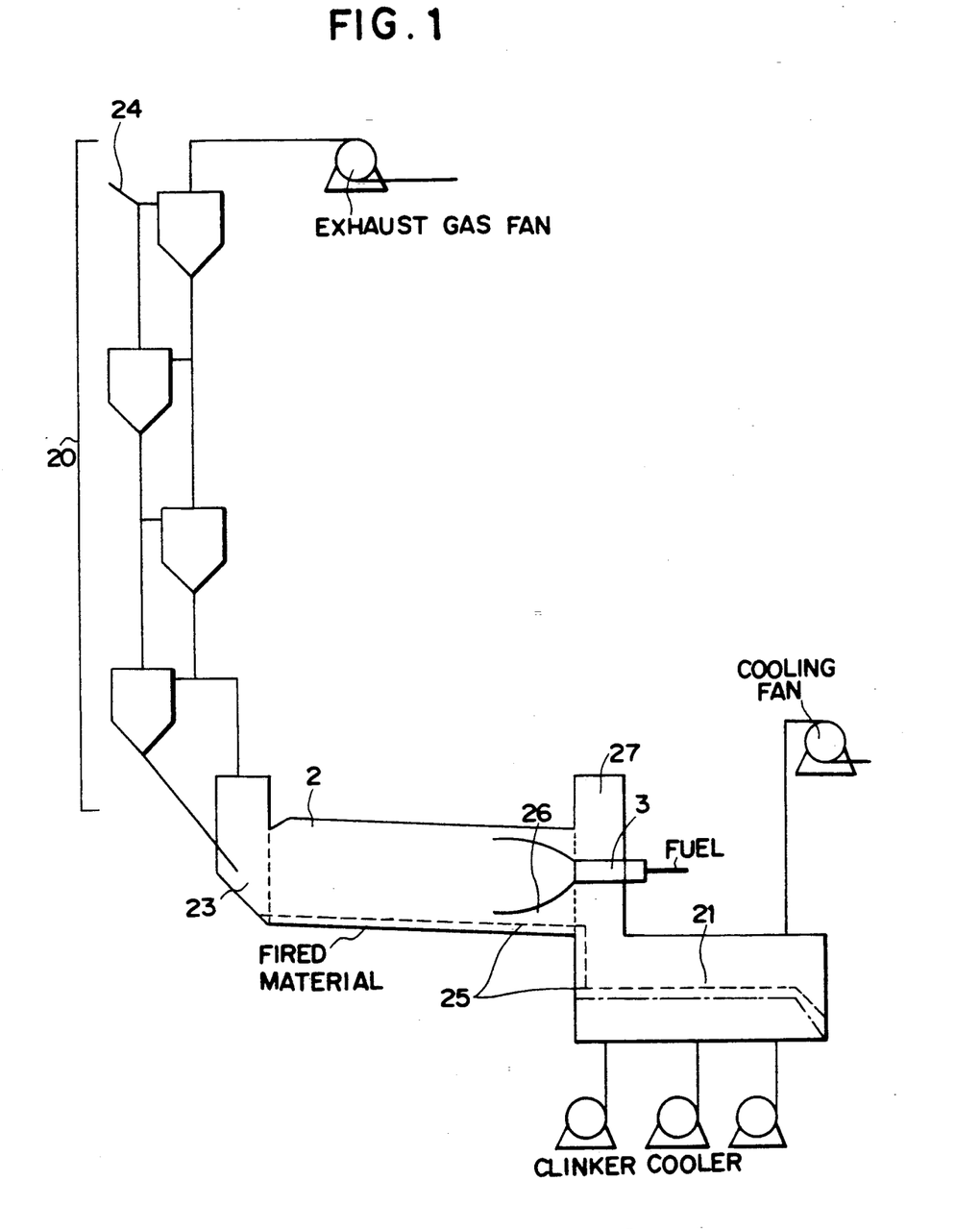
FIG. 1 shows a typical schematic view of a cement kiln to which the inventive method is applied.

FIG. 1 shows a typical schematic view of a cement kiln to which the inventive monitoring apparatus is applied.

Figure 2:
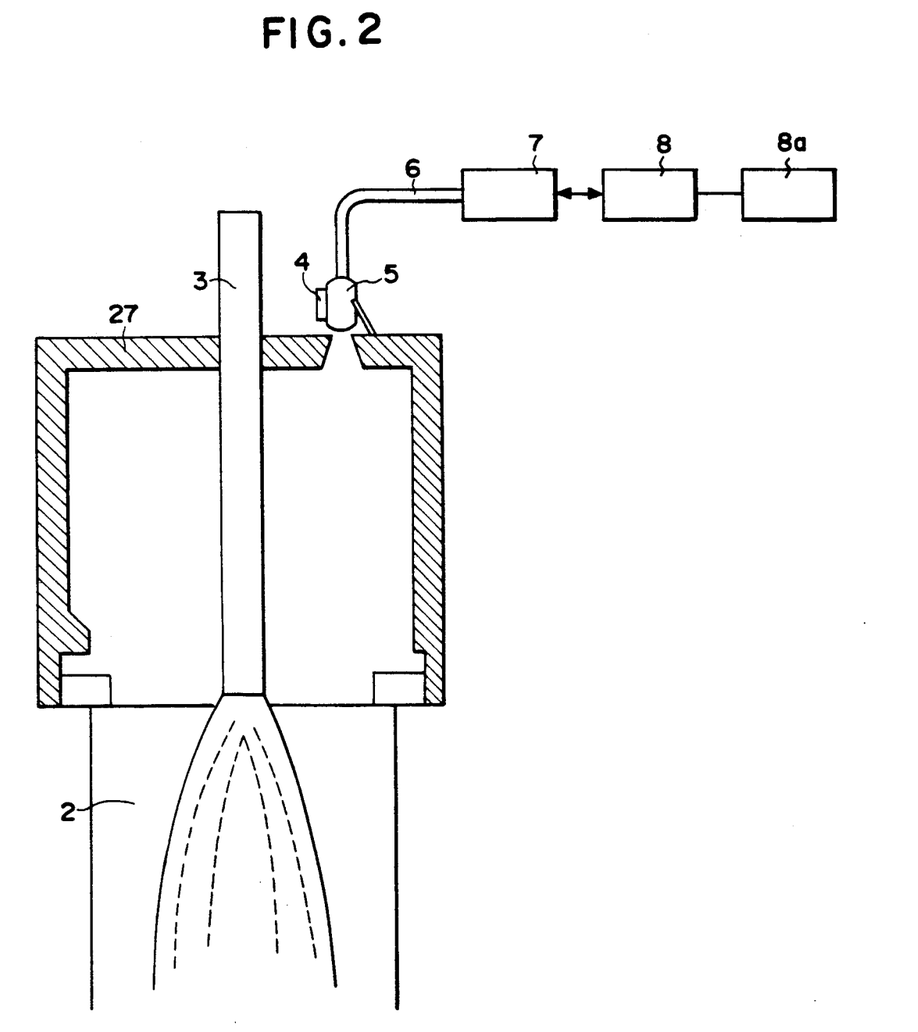
FIG. 2 illustrates schematically a structure of the cement kiln and a monitoring apparatus mounted thereon.

FIG. 2 illustrates schematically a structure of the monitoring apparatus mounted on the cement kiln.

Raw materials 24 are fed as shown in FIG. 1, from the top stage of the preheater 20, and transferred downward in the preheater 20, and are heated by exchanging heat with a high temperature exhaust gas raising in the preheater, and the heated materials are supplied from an inlet 23 of the kiln into the rotary tube of the kiln. The materials 24 fed into the rotary kiln are calcined by burning gas and transferred into the kiln and finely sintered at a firing zone 26 of the kiln to produce clinker 25. The clinker 25 is discharged from an outlet of the kiln into a clinker cooler 21, in which the clinker is cooled by quenching air from a cooling fan. Air blow which have cooled fired clinker discharged at a high temperature cooling chamber 21 passes through a kiln hood 27, and enter into the kiln 2 for combustion air. A burner 3 is equipped as shown in FIG. 2, through the front wall of the kiln hood 27, and is shoot up the fuel so as to sinter the cement materials 24.

In order to monitor the firing condition in the kiln, a firing temperature, concentrations of nitrogen oxide ($NO_x$) and oxygen in the kiln exit gas, and a kiln torque supplied to the kiln have been measured for the appropriate operation of the kiln.

Further, the intensity of the spectrum profile other than the alkali absorption lines are measured and the measured values can be one of date for monitoring the firing condition in the kiln. The apparatus for measuring such intensity has the following structure as shown in FIG. 2.

FIG. 2 illustrates schematically a structure of the cement kiln and a monitoring apparatus mounted thereon. An optical head portion 5 is fixed at the front wall of a kiln hood 27, and the radiation from the interior of the kiln is collected by the optical head 5, and transmitted through an optical fiber 6, and detected or analysed by a spectrophotometer 7, and then, the processor (computer) 8 connecting to the spectrophotometer 7 will process the data obtained by the spectrophotometer 7, and output the data to the display or process computer 8a, and the output will be processed together with the other parameters such as the $NO_x$ concentration, and then, the process computer will control the feed rates of the materials and the fuel and the kiln revolution so as to maintain the appropriate firing condition in the kiln.

Figure 3:
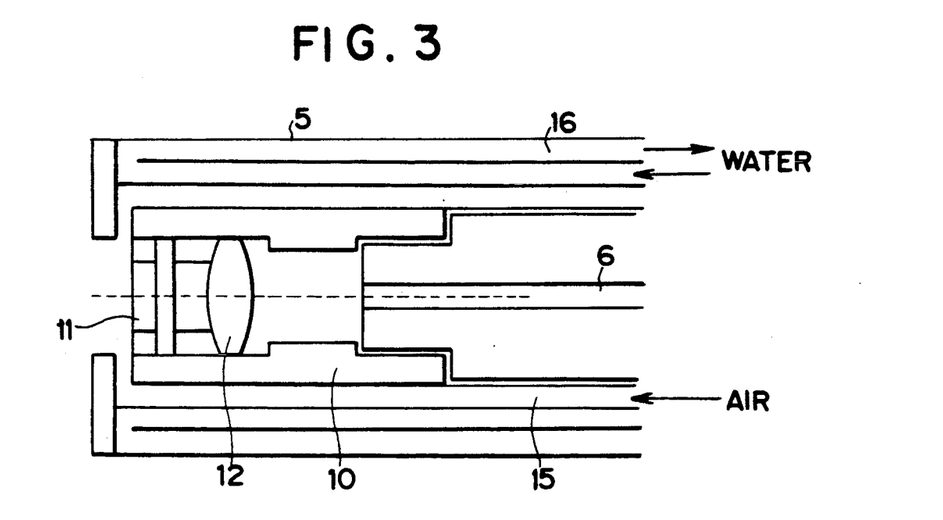
FIG. 3 shows schematically a sectional view of the optical head used for the inventive monitoring apparatus.

FIG. 3 shows schematically a sectional view of the optical head 5 used for the inventive monitoring apparatus.

The optical head 5 has a condenser lens 12 to gather only the radiation from the target material and so as to avoid receiving the radiation from other than the target (object) to be measured, and a heat resistant protection glass plate 11 to protect the lens from the high temperature. The condenser lens, the protection glass plate 11 and the optical fiber 6 are fixed by a lens holder 10, and then, it is easy to dismantle and change the lens and the other elements.

In order to protect the collecting head portion from the high temperature, a water cooling tube 16 is mounted over the outside of the optical head 5. Further, an air passage 15 is provided for air purging on the surface of the glass plate 11, between the water cooling tube 16 and the lens holder 10 so as to protect the lens from the high temperature and the contaminant from the kiln.

The optical head portion is preferably mounted on a rotatable or pivotable mounting structure provided on the front kiln hood, which can facilitate to aline the optical head with the direction of the position to be measured.

Figure 4:
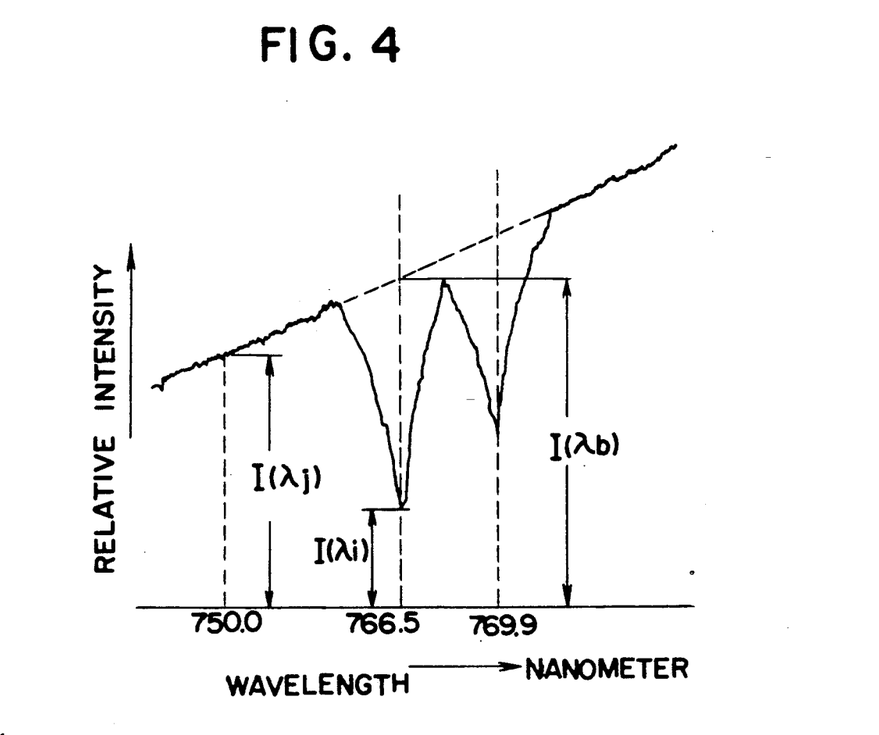
FIG. 4 is a typical graph showing the relative intensity of the radiation spectrum plotted against the wavelength (the absorption spectrum of potassium when the kiln is operated at a steady state), wherein the intensity of the radiation is shown in the neighbourhood of the potassium ion absorption wavelength 766.5 nanometer and 769.9 nanometer, and I ($\lambda$ i) is an real intensity at the potassium absorption wavelength of 766.5 nanometer, and I($\lambda$ j) is a real intensity of the radiation at the neighborhood thereof(750 nanometer), and I($\lambda$ b) is the intensity calculated from the line interpolated from the neighborhood thereof.

FIG. 4 is a typical graph showing the relative intensity of the radiation spectrum plotted against the wavelength (i.e. the absorption spectrum of potassium when the kiln is operated at a steady state. The intensity of the radiation is shown in the neighbourhood of the potassium ion absorption wavelength 766.5 nanometer and 769.9 nanometer, and I ($\lambda$ i) is an real intensity at the potassium absorption wavelength of 766.5 nanometer, and I ($\lambda$ j) is a real intensity of the radiation at the neighborhood thereof, and I ($\lambda$ b) is the intensity calculated from the line interpolated from the neighborhood thereof. The absorption intensity of alkali spectrum measured on the radiation from the kiln is calculated from the following equation.

$$Pi = [I(\lambda i) - I(\lambda b)]/I(\lambda j)$$

wherein I ($\lambda$ i) is a measured value at the wavelength of 589.6 nanometer when sodium absorption line is used, and at the wavelength of 766.5 nanometer and 769.9 nanometer when the potassium absorption line is used. I ($\lambda$ b) is an intensity which is calculated by interpolating from the measured intensity of the neighborhood to the wavelength $\lambda$ i, e.g. 766.5 nanometer, which means the radiation intensity when the absorption of potassium spectrum does not exert. I ($\lambda$ j) is the intensity of the radiation at wavelength of 600 nanometer for sodium absorption line, and at wavelength of 750 nanometer for potassium absorption line.

Figure 5:
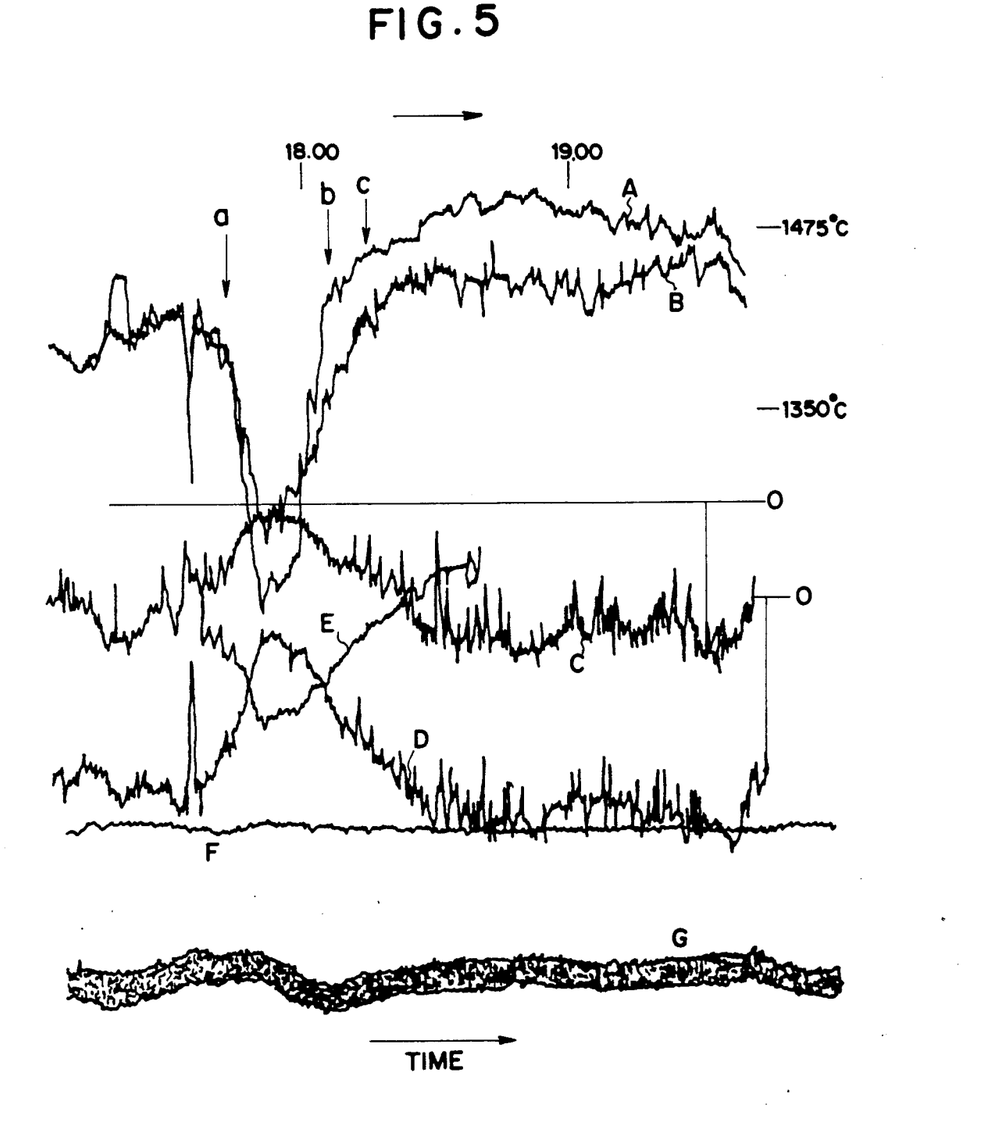
FIG. 5 is a graph of the real measurement on a real cement kiln, wherein the temperature measured by a pyrometer (curve A), the temperature measured by the inventive apparatus (curve B), the relative absorption intensity of the radiation at sodium absorption wavelength (curve C), the relative absorption intensity of the radiation at potassium absorption wavelength (curve D), the concentration of $NO_x$ in the exhaust gas (curve E), the feed rate of the cement material (curve F), and the current (kiln torque) supplied to the kiln (curve G).

FIG. 5 is a graph of the real measurement on a real cement kiln, which was carried out by periodical measurement at an interval of 20 seconds, wherein the temperature measured by a pyrometer (curve A), the temperature measured by the inventive apparatus (curve B), the relative absorption intensity of the radiation at sodium absorption wavelength (curve C), the relative intensity of the radiation at potassium absorption wavelength (curve D), the concentration of $NO_x$ in the exhaust gas (curve E), the feed rate of the cement material (curve F), and the current (kiln torque) supplied to the kiln (curve G). The change of the absorption intensity by alkali atom(s) Pi is dependent on the absorption spectrum intensity at the sodium absorption wavelength (curve C), and the absorption spectrum intensity at the potassium absorption (curve D).

The measurement was carried out by using a high resolution multidetector MPCD-110A available from Outsuka Electron Co., as a spectrophotometer, and an optical fiber UT-600 available from Mitsubishi Wire Co.

As shown in a graph of FIG. 4, the line spectrum at sodium line or potassium line is an absorption spectrum when the operation is in a steady state. But, when the operation is disordered (the kiln is upset) and becoming to non-steady state, the intensity of the absorption spectrum is smaller. Then, when the operation becomes in steady state, the intensity of the absorption spectrum will return, and higher.

As shown in the graph of FIG. 5, at the point a of time, the operation begun to be disordered, in that the temperature curve A measured by a pyrometer was lowered, and the other measured values, i.e. parameters including the absorption intensity of the absorption spectrum at sodium line and potassium line, i.e. the curves C and D, and the curve E (the concentration of $NO_x$ in the kiln exit gas). The temperature curve A seems to be recovered at the point b. In contrast, the other parameters were not recovered at the point b. For example, the driving current(kiln torque) curve G was not recovered at the point b, and the concentration curve (E) of $NO_x$ was not recovered. Further, the absorption intensity in the absorption spectrum at sodium line and potassium line (curves C and D) do not seem to be recovered at the point b. At the point c, while the temperature curve A measured by the conventional pyrometer seemed to be completely recovered to the steady state, the operation or the firing condition or the state in the kiln did not seem to be recovered in view of the spectrum absorption intensity curves C and D at sodium line and potassium line as measured in accordance with the present invention.

It can be concluded from the above mentioned fact as shown in FIG. 5 that the absorption intensity of absorption spectrum at sodium line and potassium line can be information to judge the firing state or condition in the kiln.

The absorption intensity in the absorption spectrum at alkali lines can be changed depending on the intensity of the radiation from the kiln when measured, and therefore, the reliability of the data will be a problem, should be confirmed. Then, the ratio to I ($\lambda$ j) which means the intensity of the radiation at the neighborhood wavelength without the special element line was calculated to determine the Pi value. However, the correct Pi value can be calculated upon the assumption of I ($\lambda$ j) = 1, and can be used as a parameter to judge the firing state or condition in the kiln.

Spectrum Change due to Alkali Concentration

The influence of the alkali concentration to the spectrum intensity was reviewed by measuring the spectrum intensity of the radiation at the neighborhood of the burner gun, when a burner nozzle was inserted at the position of the center of the burner.

The used fuel was a powdered coal, and the potassium content therein is one order of magnitude less than the potassium content in the clinker. The line spectrum of potassium obtained by only the combustion of the fuel is emission spectrum, the width of which is about 4.5 nanometer with double lines.

While the cement kiln was operated at very low revolution rate, with little supply of the materials to nearly stop the movement of the material in the kiln, the radiation from the kiln was detected or measured to result in emission intensity at the potassium lines. The width of the resulting emission spectrum was about 8 to 9 nanometer. It can be assumed and be confirmed upon considering the potassium contents in the fired clinker and in the powdered coal that the change of the potassium content will exert influence on the width of the spectrum, and does not have effect on the intensity of the spectrum.

EXAMPLE 2

The optical heads as shown in FIG. 2 were mounted respectively in the two (or more) kilns, so as to measure the absorption spectrum intensity on each of the kilns, and the assembly of the optical fibers connecting each head with a spectrophotometer was made as shown in FIG. 7(A). An optical switch 30 of type FS 21 available from Mitsubishi Electric Co. Ltd. was used to connect each of optical cables 6, i.e. connecting a terminal $P_1$ to a fiber $6_1$ from an optical head $5_1$ to monitor a cement kiln A, and a terminal $P_3$ to a fiber $6_2$ from an optical head $5_2$ to monitor a kiln B, and a terminal $P_2$ to a spectrophotometer 7, and the optical switch 30 was operated by a computer.

When the switch 30 is on, the light from the kiln A is transmitted to the spectrophotometer 7. When the switch 30 is off, the radiation from the kiln B is transmitted to the spectrophotometer 7. The switching interval was 20 seconds. Further, more than two kilns can be monitored by the inventive apparatus.

As shown in FIG. 7B, optical switches 30-1, 30-2 and 30-3 can be used, and two or more switches can be combined in parallel or series form, and then, more number of the kilns or targets A, B, C and D can be measured or monitored by only one monitor or spectrophotometer 7 as shown in FIG. 7B.

The change of intensity at the alkali absorption lines was measured for monitoring the firing condition in the kiln. Such monitoring method can not be affected by dusty atmosphere in the kiln containing the sintered clinker powder and dust. Especially during the transition time where the operation of the kiln was transferred from steady state to non-steady state, or from non-steady state to steady state, the firing condition in the kiln can be accurately and finely monitored, and controlled, and then, the kiln can be operated finely controllably by coping correctly with the sudden change of the operation parameters or conditions.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

We claim:

1. An apparatus for monitoring the firing condition of a cement clinker in a kiln, said apparatus comprising:
    (a) an optical head equipped at a kiln hood of a kiln to collect radiation from the clinker being fired in the kiln;
    (b) an optical fiber cable having a first end mounted in said optical head for receiving said radiation and transmitting the collected radiation from said optical head;
    (c) a spectrophotometer connected to a second end of said optical fiber cable for measuring a spectrum of the radiation; and
    (d) a processor connected to said spectrophotometer for calculating a degree of absorption or emission of radiation which is emitted by said clinker being fired in said kiln, wherein the resulting degree of absorption or emission is used to monitor the temperature and the sintering condition of said clinker by comparing a baseline level of said spectrum to a measured profile using sodium and potassium wavelength measurements.

2. An apparatus for monitoring the firing condition of a clinker in a kiln, in accordance with claim 1, wherein said processor is connected to a process computer which controls, the revolution of the kiln, and the feed rate of materials to the kiln, through the value of said degree of radiation absorption or emission.

3. An apparatus for monitoring the firing condition of a clinker in a plurality of kilns, comprising:
 (a) an optical head equipped at a kiln hood of a kiln to collect radiation from the clinker being fired in the kiln;
 (b) a first optical fiber cable having a first end and a second end, the first end mounted in said optical head for receiving said radiation and transmitting the collected radiation from said optical head and said second end connected to an optical transfer switch;
 (c) a spectrophotometer for measuring the spectrum of the radiation connected to a second end of a second optical fiber cable, the optical transfer switch connected to the spectrophotometer through a first end of the second optical fiber cable for; and
 (d) a processor connected to said spectrophotometer for calculating a degree of absorption or emission of radiation which is emitted by said clinker being fired in said kiln, wherein the resulting degree of absorption or emission is used to monitor the temperature and the sintering condition of said clinker by comparing a baseline level of said spectrum to a measured profile using sodium and potassium wavelength measurements;

wherein an optical head and an optical fiber cable are provided respectively on each of a plurality of said kilns, and said transfer switch is provided along an optical fiber cable for selecting an optical head thereby measuring an intensity profile of the radiation emitted by a clinker in a selected kiln, thereby allowing for the monitoring of conditions in a number of kilns.

4. An apparatus for monitoring the firing condition of a clinker in a plurality of kilns, in accordance with claim 3, wherein said processor is connected to a process computer which controls the revolution of the kiln, and the feed rate of materials to the kiln, through the value of said degree of radiation absorption or emission.

* * * * *